United States Patent [19]
Schuster

[11] 3,982,423
[45] Sept. 28, 1976

[54] MUCUS TESTING PROCESSES AND DEVICES

[75] Inventor: Samuel R. Schuster, Wellesley, Mass.

[73] Assignee: Ovutime, Inc., Wellesley, Mass.

[22] Filed: Nov. 12, 1974

[21] Appl. No.: 523,047

Related U.S. Application Data

[63] Continuation-in-part of Ser. No. 462,298, April 19, 1974, abandoned, which is a continuation-in-part of Ser. No. 433,767, Jan. 16, 1974, abandoned, which is a continuation-in-part of Ser. No. 300,187, Oct. 24, 1972, and a continuation-in-part of Ser. No. 472,611, May 23, 1974, which is a continuation-in-part of said Ser. No. 300,187.

[52] U.S. Cl. ............................. 73/54; 23/230 B; 73/9; 128/2 W
[51] Int. Cl.² ....................................... G01N 33/16
[58] Field of Search ............... 73/54, 59, 60, 9, 10, 73/53; 128/2 W; 23/230 B

[56] References Cited
UNITED STATES PATENTS

| | | | |
|---|---|---|---|
| 1,184,880 | 5/1916 | Schleher, Jr. .......................... 73/10 |
| 2,427,289 | 9/1947 | Lancaster ............................. 73/9 X |
| 2,878,670 | 3/1959 | Martin .................................. 73/60 |
| 2,953,016 | 9/1960 | Seitz, Jr. ............................... 73/60 |
| 3,115,034 | 12/1963 | De Hart ............................. 73/60 X |
| 3,552,198 | 1/1971 | Friedland ............................. 73/9 X |

OTHER PUBLICATIONS

Benis, A. M. et al., *Rheology of Biological Systems*, Ill., Thomas, 1973, Chapter 9, pp. 218–259.

*Primary Examiner*—Herbert Goldstein
*Assistant Examiner*—Joseph W. Roskos
*Attorney, Agent, or Firm*—Morse, Altman, Oates & Bello

[57] ABSTRACT

A mucus sample from a bodily cavity is introduced between inner and outer bearing members, one of which is fixed, one of which is biased, and both of which have bearing surfaces of predetermined surface finish. Relative mechanical movement of the members indicates menstrual cycle phase.

7 Claims, 10 Drawing Figures

MUCUS TESTING PROCESSES AND DEVICES

RELATED APPLICATION

The present application is a continuation-in-part of my earlier application Ser. No. 462,298, filed Apr. 19, 1974, now abandoned, which in turn is a continuation-in-part of my earlier application Ser. No. 433,767, filed Jan. 16, 1974, now abandoned which in turn is a continuation-in-part of my earlier application Ser. No. 300,187, filed Oct. 24, 1972. The present application also is a continuation-in-part of my earlier application Ser. No. 472,611, filed May 23, 1974, which in turn is a continuation-in-part of aforesaid application Ser. No. 300,187, filed Oct. 24, 1972. The present invention also is related to application Ser. No. 629,700, filed Nov. 7, 1975, which is a continuation of aforesaid application Ser. No. 472,611, filed May 23, 1974.

BACKGROUND OF THE INVENTION

The present invention relates to processes and devices for determining the phase of the menstrual cycle and, particularly, to indicating the rheological properties of bodily mucus, particularly cervical mucus and/or oral mucus, in order to predict the inception and to indicate the presence of ovulation. The present invention thus is concerned with conception control. It has been found that mucus samples from the vaginal and oral cavities undergo distinct in-phase rheological changes during the menstrual cycle. Although the changes in the cervical mucus are much more noticeable than the changes in the oral mucus, both changes are readily determinable. During the immediate pre-ovulatory phase, for a period of one to three days under estrogen domination, the mucus is profuse and watery. During the postovulatory phase, under progestation, the mucus becomes less abundant and more viscous. In healthy women with normal menstrual cycles, as is well documented in the medical literature, ovulation usually occurs between the 12th and 14th day prior to the next menstrual period (and not after the preceding period). Specifically, cervical mucus is most hydrated at the time of ovulation, containing 97 to 98% water, and is relatively dehydrated at other times, containing only 80 to 90% water. The solid residue after desiccation may range from 2% during ovulation to 20% at other times, a ten fold increase. Predicting ovulation on the basis of the preceding menstrual period by counting the number of days elapsed between the end of the preceding period and the presumed mid-cycle ovulatory phase (the rhythm method) is prone to errors because it is impossible to predict the onset of the next menstrual period. It is possible to predict ovulation on the basis of hormonal changes in the blood or chemical changes in the mucus but present procedures for such analyses are useful only in special cases because the procedures for such analyses are useful only in special cases because the procedures involved are lengthy and costly. At present, there are no known reliable on-the-spot techniques capable of providing the information necessary for prediction or confirmation of ovulation during or immediately following examination of a patient.

SUMMARY OF THE INVENTION

The primary object of the present invention is to provide processes and devices, for testing bodily mucus, by introducing the mucus between inner and outer bearing members, one of which is fixed, one of which is biased, and both of which have bearing surfaces of predetermined surface finish, the resulting presence or absence of mechanical movement constituting an indicium of ovulation. The inner and outer bearing members are individually separable from each other and from a support so that they can be sterilized or replaced. The motions between the bearing members are either rotational or reciprocal. Ordinarily, the mucus is supplied to one of the bearing surfaces while the bearing members are dissembled from each other and the mucus is extruded between the bearing surfaces when they are assembled with each other. In one form, one of the bearing members is fixed on a suitable support and the other is provided with a biasing member, e.g. a weight or a spring, which exerts sufficient force to cause relative movement when the highly fluid mucus has been sampled during the ovulatory phase but insufficient force to cause relative movement when the viscous mucus has been sampled at other times during the menstrual period. In another form, one of the bearing members is an extension of an elongated probe for insertion into the vaginal cavity and retrieval on the extension of a cervical mucus specimen. In accordance with the present invention, it has been discovered that the foregoing operation requires that the bearing members have inner and outer bearing surfaces, each characterized by a surface finish having valleys and peaks of from 8 to 125 microinches in average valley to peak height. such a surface finish, in various embodiment, is provided by machining or etching random valleys and peaks or machining or etching regularly spaced prismatic facets or the like. It is believed that this specific surface roughness controls slippage of the mucus with respect to the bearing surfaces and ensures the occurence of predetermined shear within the mucus interior.

Other objects of the present invention will in part be obvious and will in part appear hereinafter.

The invention accordingly comprises the processes and devices, together with their steps, parts and interrelationships, which are exemplified in the present disclosure, the scope of which will be indicated in the appended claims.

BRIEF DESCRIPTION OF THE DRAWINGS

For a fuller understanding of the nature and objects of the present invention, reference is made to the following detailed description, which is to be taken in connection with the accompanying drawings, wherein.

DETAILED DESCRIPTION

Figure 1:
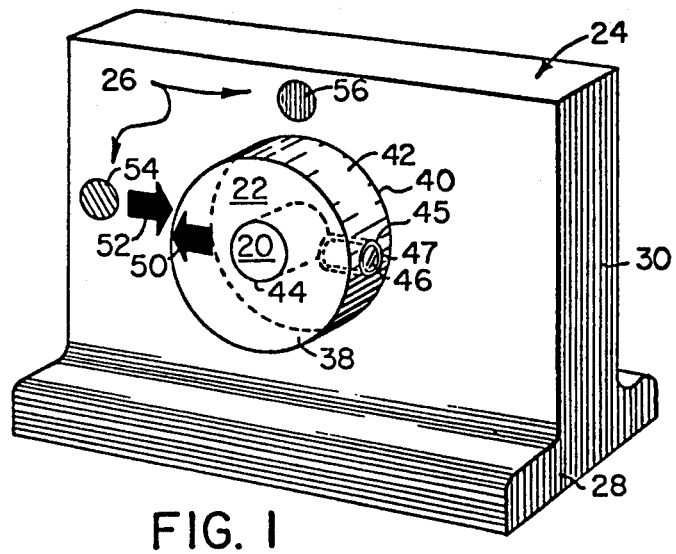
FIG. 1 is a perspective view of a device embodying the present invention, with parts assembled for the performance of certain steps of a process of the present invention.

Generally, the device of FIG. 1 comprises an inner bearing member 20, an outer bearing member 22, a biasing member 46, a support 24, an indicia 26. Support 24, which includes a horizontal base 28 and an upright plate 30, is composed of a suitable plastic such as methyl methacrylate or polycarbonate. Plate 30 is provided centrally with a horizonally extending notch 32 having an axis that is perpendicular to the faces of plate 30 and a rectangular cross section.

Inner bearing member 20 is in the form of a short cylindrical rod having along its axis, a rearward extension or key 34 and a forward cylindrical bearing surface 36. Key 34, which snugly and removably fits into slot 32, maintains a horizontal orientation of the axis of bearing member 20 when bearing member 20 and support 24 are assembled. Outer bearing member 22 is in the form of a disc having an axis, along which are disposed forward and rearward parallel flat faces 38,40, an outer cylindrical periphery 42 and an inner cylindrical bearing surface 44. Outer bearing surface 36 and inner bearing surface 44 snugly and rotatably fit each other when bearing elements 20 and 22 are assembled.

In accordance with the present invention, each of bearing surfaces 36,44 requires a surface finish ranging from 8 to 125 microinches (approximately 0.2 to 3.2 microns) in average valley to peak height. Also, the spacing of tolerance between the bearing surfaces ranges from 0.01 to 10.0 mils (approximately 0.254 to 254.0 microns) and preferably from 1 to 5 mils (approximately 25.4 to 127.0 microns). Preferably the axial thickness of outer bearing member 22 ranges from ¼ to 2 inches (approximately 6.35 to 50.8 mm). Preferably each of the bearing members is composed of a dimensionally stable, sterilizable material, for example, a vitreous material such as glass, a metallic material such as stainless steel, or a plastic material such as methyl methacrylate.

Extending through periphery 42 into the bore of outer bearing member 22 is a bore 45. Frictionally secured within bore 45 is an internally threaded sleeve 47 composed, for example, of plastic or metal. Turned into sleeve 47 is weighted plug 46, which is externally threaded and which is composed, for example, of metal or the like. Plug 46 has an external screwdriver slot by which the position of the plug with respect to the axis of the outer bearing member can be adjusted precisely.

Indicia 26 include an outwardly directed arrow 50 on outer bearing member 22 and an inwardly directed arrow 52 on plate 30. When the inner and outer bearing members are assembled with mucus between their bearing surfaces, weighted plug 46 is in a position to cause rotary motion of the outer bearing member with respect to the inner bearing member. Adjacent to arrow 52 on plate 30 is a green spot 54 and adjacent to external bearing member 22 at 90° from green spot 54 is a red spot 56. The arrangement is such that when the mucus between the bearing surfaces is relatively watery, weighted plug 46 rotates outer bearing member 22 in a clockwise direction so that arrow 50 points toward red spot 56. On the other hand, when the mucus is relatively viscous, weighted plug 46 is incapable of rotating outer bearing member 22 so that arrow 50 remains pointed toward green spot 54.

One process of the present invention involves the use of sterile inner and outer bearing members 20,22 as follows. First, inner bearing member 20 is assembled with plate 30 by inserting key 34 into slot 32. Next, a sample of cervical mucus is obtained by inserting a disposable probe 60, having an elastomeric scoop 62 at its extremity, through the vaginal cavity into contact with the cervix in order to retain a sample of cervical mucus 63. Next, this cervical mucus is transferred to one of bearing surfaces 36, 44 and the inner and outer bearing members are assembled by fitting outer bearing member 22 onto inner bearing member 20, the arrangement being such that the cervical mucus is extruded between the bearing surfaces. Next outer bearing member 22 is rotated manually a predetermined number of times, usually from one to three times, until arrows 50,52 are aligned. Then outer bearing member 22 is released. Finally, the rest position of arrow 50 relative to green spot 54 and red spot 56 is indicative of the presence or absence of ovulation.

In an alternative process, oral mucus, i.e. saliva is removed from the mouth by an eye dropper 64 having a tube 66 with a restricted end 68 and an elastomeric bulb 70. Here, saliva is applied to one of bearing surfaces 36,44 simply by manually squeezing bulb 70 and extruding saliva through opening 68. This process otherwise is identical to that described above in connection with cervical mucus.

Figure 5:
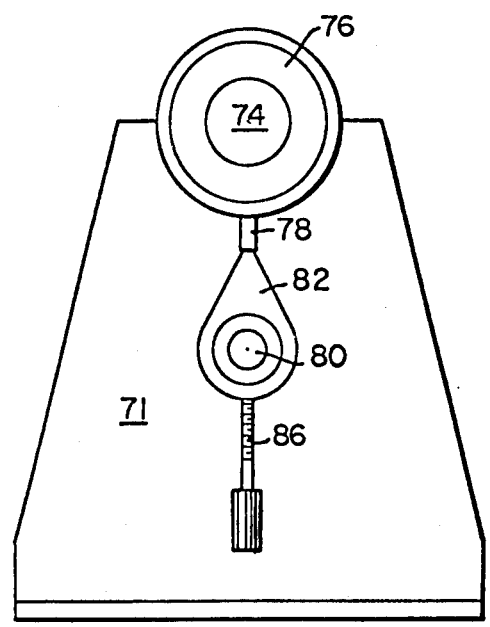
FIG. 5 is a front elevation of another device embodying the present invention.
Figure 6:
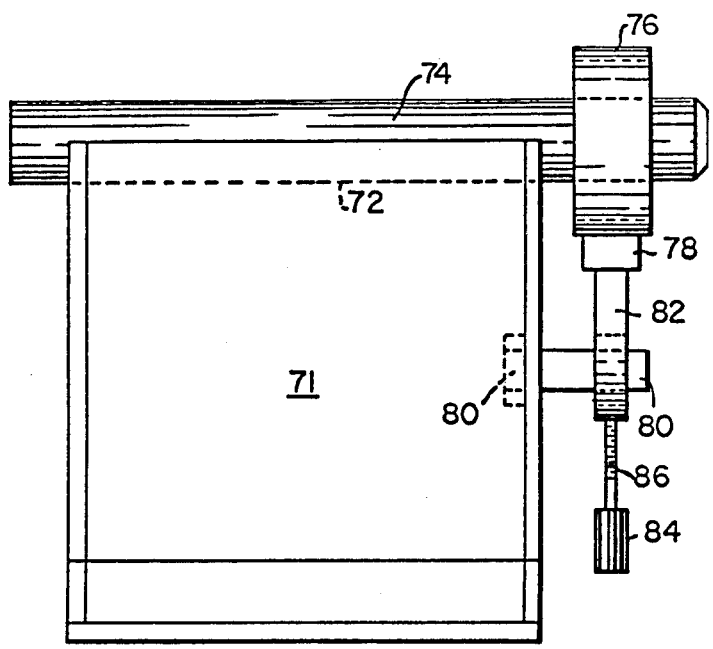
FIG. 6 is a side elevation of the device of FIG. 5.
Figure 7:
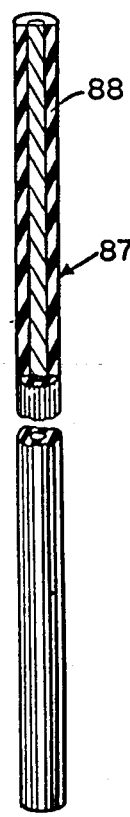
FIG. 7 is a cross-sectional view, along the axis, of a component useful in connection with the operation of the device of FIG. 6.

The device of FIGS. 5, 6, and 7 includes a base 71 having a bearing bed 72. Resting on bearing bed 72 is a rod 74, which extends forwardly to receive a ring 76. The forward extremity of rod 74 and the internal periphery of ring 76 provide bearing surfaces of the type described above for the receipt of mucus. Depending from ring 76 is a tripping element 78. Extending forwardly from base 71 is a cantilever shaft 80 on which is journaled a finger 82 that is biased into contact with tripping element 78. The bias is effcted by a weight 84, which is carried by a threaded screw 86 and which is adjustable by rotation of the threaded screw. Associated with rod 74 is a bow 87, in the form of a rod having a rubber outer surface 88. Bow 87, when manually advanced from one end to the other in contact with a surface or rod 74, rotates rod 74 a predetermined number of rotational cycles.

In operation, with ring 76 removed, mucus is supplied to the forward extremity of rod 74 by a scoop or an eyedropper of the types described in connection with the device of FIG. 1. Thereafter ring 76 is fitted onto the end of rod 74 and bow 87 manually is stroked from one end to the other along the periphery of rod 74 in order to cause its rotation. In the event that the mucus is relatively watery, rotation or ring 76 will not occur and tripping element 78 will not be actuated. However, if the mucus is relatively viscous, rotation of rod 74 will cause tripping mechanism 78 to be actuated.

Figure 8:
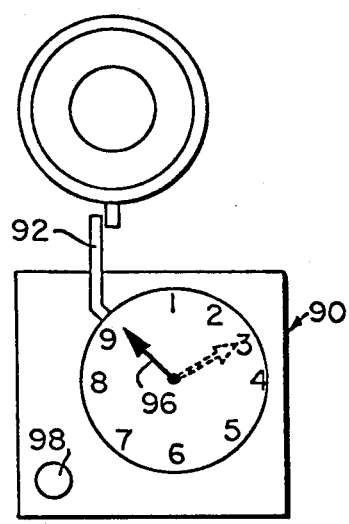
FIG. 8 is a front elevation of a further device embodying the present invention.

The embodiment of FIG. 8 is analogous to the embodiment of FIGS.5, 6, and 7 in all respects except that ripping arrangement 82, 84, 86 is replaced by a calibrated tension gage 90, which includes a tripping finger 92 that is biased by a weight or spring or the like, a memory pointer 96, and an indicator light 98.

Figure 2:
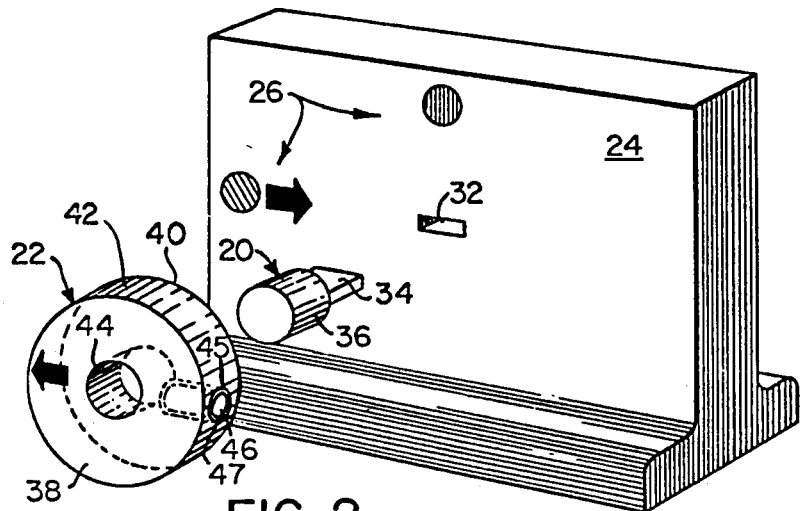
FIG. 2 illustrates the device of FIG. 1, with its parts dissembled for the performance of certain steps of a process of the present invention.
Figure 3:
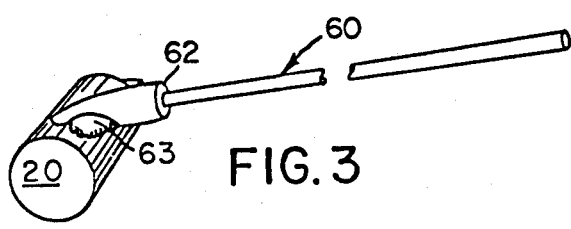
FIG. 3 illustrates an auxilliary instrument useful in the performance of certain steps of the present invention.
Figure 4:
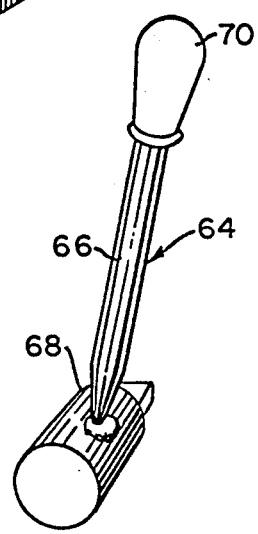
FIG. 4 illustrates another auxiliary instrument useful in accordance with the present invention.
Figure 9:
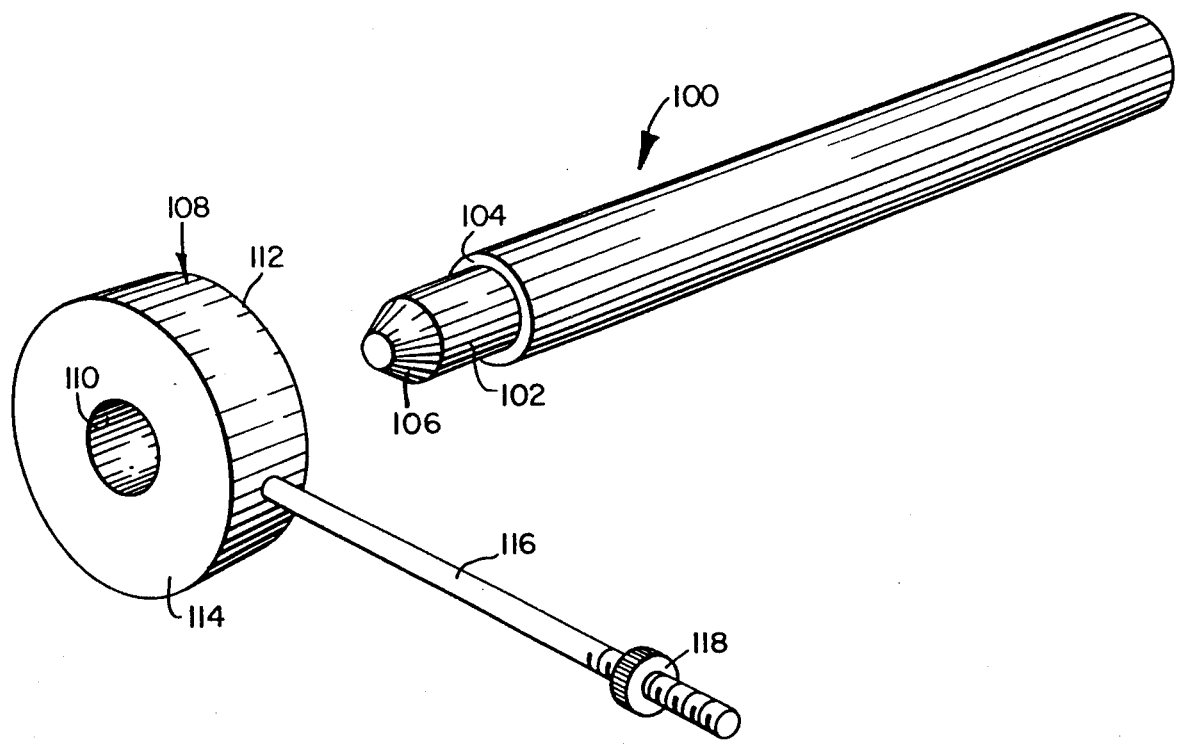
FIG. 9 is a perspective view of another device embodying the present invention, with parts dissembled for the performance of certain steps of the process of the present invention.
Figure 10:
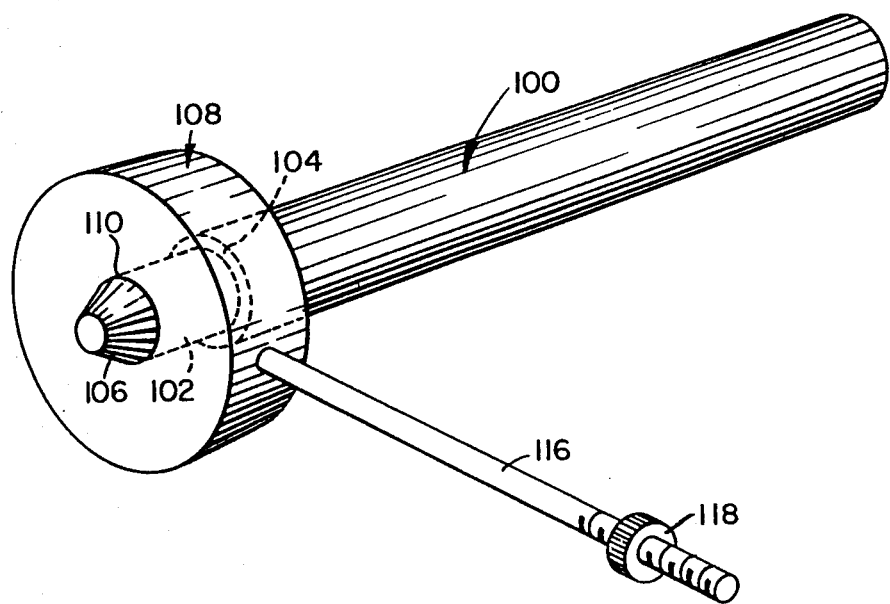
FIG. 10 is a perspective view of the device of FIG. 9, with parts assembled for the performance of other steps of the present invention.

The embodiment of FIGS. 9 and 10 includes an elongated cylindrical probe 100, at the forward extremity of which is a cylindrical extension 102 of reduced diameter that is isolated from the remainder of the probe by a shoulder 104. The forward extremity of extension 102 is rounded as at 106. Associated with probe 100 is an annulus 108 having an inner bore 110 and forward and rearward flat parallel faces 112, 114. The outer bearing surface of extension 102 and the inner bearing surface of bore 110 snugly fit each other when ring 108 and probe 100 are assembled. Extending from the periphery of ring 108 is a threaded shaft 116 having turned thereon an adjustable nut 118, the shaft and the nut serving as an adjustable torque weight. Probe 100 and ring 108 are composed of the same materials as are their counterparts in FIGS. 1 and 2. Also the dimensions and grit characteristics of extension bearing surface 102 and of bore bearing surface 110 are the same as are their counterparts in FIGS. 1 and 2.

In operation of the device of FIGS. 9 and 10, first probe 100 is inserted into the vaginal cavity so that extension 102 contacts the cervix, by which a quantity of cervical mucus is retained on the bearing surface of extension 102. Next probe 100 is withdrawn from the vaginal cavity and is assembled with ring 108 so that extension 102 is inserted into bore 110 and rearward movement of ring 108 is limited by shoulder 104. At this point cervical mucus is extruded between the bearing surfaces of bore 110 and extension 102. Then a user, while holding probe 100 horizontally in one hand, moves shaft 116 into horizontal orientation with the other hand. Finally when shaft 116 is released, rotation of ring 108 relative to probe 100, under the torque of weight 116, 118 will or will not occur. Menstrual cycle phase thereby will be indicated in accordance with the present invention.

It will be appreciated that the motion of devices herein have been shown as being rotational as opposed to reciprocable. However, the principles of the present invention apply as well to the reciprocating internal and external bearing members although such devices are less preferred. Since certain changes may be made in the present disclosure without departing from the scope of the present invention, it is intended that all matter shown in the accompanying drawings or described in the foregoing specification be interpreted in an illustrative and not in a limiting sense.

What is claimed is:

1. A device for testing mucus from a bodily cavity, said device comprising a base, inner bearing means and outer bearing means composed of glass, said inner bearing means and said outer bearing means being arranged for motion with respect to each other on said base, means for biasing said inner bearing means and said outer bearing means for said motion, and means for indicating the occurrence of said motion, said inner bearing means and said outer bearing means have inner and outer cylindrical bearing surfaces, each of said bearing surfaces having a surface finish ranging from approximately 0.2 microns to 3.2 microns in valley to peak height, the clearance between said bearing surfaces ranging from approximately 0.25 microns to 254.0 microns, said means for indicating including indicia movable with at least one of said bearing elements and indicia fixed in operation with respect to said base, said base including an upright plate having a slot, said inner bearing member having a key, said key being removably retained by said slot, one of said indicia being located on said plate and the other of said indicia being located on said outer bearing member.

2. A device for testing mucus from a bodily cavity, said device comprising a base, inner bearing means and outer bearing means composed of glass, said inner bearing means and said outer bearing means being arranged for motion with respect to each other on said base, means for biasing said inner bearing means and said outer bearing means for said motion, and means for indicating the occurrence of said motion, said inner bearing means and said outer bearing means have inner and outer cylindrical bearing surfaces, each of said bearing surfaces having a surface finish ranging from approximately 0.2 microns to 3.2 microns in valley to peak height, the clearance between said bearing surfaces ranging from approximaely 0.25 microns to 254.0 microns, said means for indicating including indicia movable with at least one of said bearing elements and indicia fixed in operation with respect to said base, said means for indicating including a calibrated tension gauge, said calibrated tension gauge being mounted on said base.

3. A device for testing mucus from a bodily cavity, said device comprising a base, inner bearing means and outer bearing means composed of glass, said inner bearing means and said outer bearing means being arranged for motion with respect to each other on said base, means for biasing said inner bearing means and said outer bearing means for said motion, and means for indicating the occurrence of said motion, said inner bearing means and said outer bearing means have inner and outer cylindrical bearing surfaces, each of said bearing surfaces having a surface finish ranging from approximately 0.2 microns to 3.2 microns in valley to peak height, the clearance between said bearing surfaces ranging from approximately 0.25 microns to 254.0 microns, said means for indicating including indicia movable with at least one of said bearing elements and indicia fixed in operation with respect to said base, said base including an elongated rod, said inner bearing member projecting from said rod and being substantially coaxial therewith, said rod providing a shoulder for limiting axial movement of said outer bearing member with respect thereto.

4. A device for testing mucus from a bodily cavity, said device comprising a base, inner bearing means and outer bearing means, said inner bearing means and said outer bearing means being arranged for motion with resect to each other on said base, means for biasing said inner bearing means and said outer bearing means for said motion, and means for indicating the occurence of said motion, said inner bearing means and said outer bearing means have inner and outer cylindrical bearing surfaces, each of said bearing surfaces having a surface finish ranging from approximately 0.2 microns to 3.2 microns in valley to peak heights, the clearance between said bearing surfaces ranging from approximately 0.25 microns to 254.0 microns, said means for indicating including indicia movable with at least one of said bearing elements and indicia fixed in operation with respect to said base, said base including an upright plate having a slot, said inner bearing member having a key, said key being removably retained by said slot, one of said indicia being located on said plate and the other of said indicia being located on said outer bearing member.

5. A device for testing mucus from a bodily cavity, said device comprising a base, inner bearing means and outer bearing means, said inner bearing means and said outer bearing means being arranged for motion with respect to each other on said base, means for biasing said inner bearing means and said outer bearing means for said motion, and means for indicating the occurrence of said motion, said inner bearing means and said outer bearing means have inner and outer cylindrical bearing surfaces, each of said bearing surfaces having a surface finish ranging from approximately 0.2 microns to 3.2 microns in valley to peak height, the clearance between said bearing surfaces ranging from approximately 0.25 microns to 254.0 microns, said means for indicating including indicia movable with at least one of said bearing elements and indicia fixed in operation with respect to said base, said means for indicating including a calibrated tension gauge, said calibrated tension gauge being mounted on said base.

6. A device for testing mucus from a bodily cavity, said device comprising a base, inner bearing means and outer bearing means, said inner bearing means and said outer bearing means being arranged for motion with respect to each other on said base, means for biasing said inner bearing means and said outer bearing means for said motion, and means for indicating the occurrence of said motion, said inner bearing means and said outer bearing means have inner and outer cylindrical bearing surfaces, each of said bearing surfaces having a surface finish ranging from approximately 0.2 microns to 3.2 microns in valley to peak height, the clearance between said bearing surfaces ranging from approximately 0.25 microns to 254.0 mirons, said mans for indicating including indicia movable with at least one of said bearing elements and indicia fixed in operation with respect to said base, said base including an elongated rod and stop means, said inner bearing member projecting from said rod and being substantially coaxial therewith, said stop means limiting axial movement of said outer bearing member with respect to said rod.

7. A device for testing mucus from a bodily cavity, said device comprising a base, inner bearing means and outer bearing means, said inner bearing means and said outer bearing mean being arranged for motion with respect to each other on said base, means for biasing said inner bearing means and said outer bearing means for said motion, and means for indicating the occurrence of said motion, said inner bearing means and said outer bearing means have inner and outer cylindrical bearing surfaces, each of said bearing surfaces having a surface finish ranging from approximately 0.2 microns to 3.2 microns in valley to peak height, the clearance between said bearing surfaces ranging from approximately 0.25 microns to 254.0 microns, said means for indicating including indicia movable with at least one of said bearing elements and indicia fixed tin operation with respect to said base, said base including an elongated rod, said inner bearing member projecting from said rod and being substantially coaxial therewith, said rod including means for limiting axial movement of said outer bearing member with respect to said rod.

* * * * *